United States Patent
Holopainen et al.

(10) Patent No.: US 9,585,564 B2
(45) Date of Patent: Mar. 7, 2017

(54) WIRELESS SKIN TEMPERATURE MEASUREMENTS IN DIVING

(71) Applicants: Reima K. Holopainen, Zufikon (CH); Jari M. A. Tiira, Lenzburg (CH)

(72) Inventors: Reima K. Holopainen, Zufikon (CH); Jari M. A. Tiira, Lenzburg (CH)

(73) Assignee: Johnson Outdoors Inc., Racine, WI (US)

(*) Notice: Subject to any disclaimer, the term of this patent is extended or adjusted under 35 U.S.C. 154(b) by 606 days.

(21) Appl. No.: 14/075,629

(22) Filed: Nov. 8, 2013

(65) Prior Publication Data

US 2014/0148710 A1    May 29, 2014

Related U.S. Application Data

(60) Provisional application No. 61/731,140, filed on Nov. 29, 2012.

(51) Int. Cl.
| | | |
|---|---|---|
| *A61B 5/00* | (2006.01) | |
| *A61B 5/01* | (2006.01) | |
| *B63C 11/32* | (2006.01) | |
| *A61B 5/0205* | (2006.01) | |
| *A61B 5/024* | (2006.01) | |
| *B63C 11/02* | (2006.01) | |

(52) U.S. Cl.
CPC ........... *A61B 5/0008* (2013.01); *A61B 5/01* (2013.01); *B63C 11/32* (2013.01); *A61B 5/024* (2013.01); *A61B 5/02055* (2013.01); *A61B 5/681* (2013.01); *B63C 2011/021* (2013.01)

(58) Field of Classification Search
CPC ......... A61B 5/01; A61B 5/015; A61B 5/0008; A61B 5/681; A61B 5/02055; A61B 5/742; A61B 5/7228; B63C 11/32; B63C 2011/021
See application file for complete search history.

(56) References Cited

U.S. PATENT DOCUMENTS

| | | |
|---|---|---|
| 3,611,332 A | 10/1971 | Slater |
| 5,806,514 A | 9/1998 | Mock et al. |
| 6,360,182 B1 | 3/2002 | Hales |

(Continued)

FOREIGN PATENT DOCUMENTS

| | | |
|---|---|---|
| EP | 2075189 A1 | 7/2009 |
| GB | 2368705 A | 5/2002 |

(Continued)

*Primary Examiner* — Max Hindenburg
(74) *Attorney, Agent, or Firm* — Reinhart Boerner Van Deuren P.C.

(57) ABSTRACT

A dive computer system that utilizes a direct skin temperature measurement is provided. The dive computer system includes a measurement device that includes a temperature sensor and is attached to a strap. The strap is placed around a diver's chest and configured to measure the diver's skin temperature. The skin temperature is wirelessly transmitted to a dive computer that utilizes a dive algorithm to determine compartment inert gas saturation and desaturation. The dive algorithm determines an updated skin perfusion factor that is in turn utilized to determine an updated half time for the skin compartment for inert gas desaturation and a pressure tolerance for the skin compartment for inert gas saturation.

8 Claims, 6 Drawing Sheets

(56) References Cited

U.S. PATENT DOCUMENTS

| | | | |
|---|---|---|---|
| 6,847,913 B2 | 1/2005 | Wigley et al. | |
| 6,895,961 B1 | 5/2005 | Todorov | |
| 6,904,382 B2 | 6/2005 | Hayafune | |
| 7,144,198 B2 | 12/2006 | Hirose et al. | |
| 7,310,549 B1 | 12/2007 | Angelini et al. | |
| 7,383,150 B2 * | 6/2008 | Angelini | B63C 11/02 405/186 |
| 7,481,773 B1 | 1/2009 | Dorroh et al. | |
| 7,497,216 B2 | 3/2009 | Forsyth et al. | |
| 7,625,117 B2 | 12/2009 | Haslett et al. | |
| RE42,218 E | 3/2011 | Magine et al. | |
| 8,144,547 B2 | 3/2012 | Plancon et al. | |
| 9,254,900 B2 * | 2/2016 | Hollis | B63C 11/02 |
| 9,320,431 B2 * | 4/2016 | Imran | A61B 5/0002 |
| 2006/0122473 A1 | 6/2006 | Kill et al. | |
| 2006/0201508 A1 | 9/2006 | Forsyth et al. | |
| 2007/0205903 A1 | 9/2007 | diMarzo et al. | |
| 2007/0239038 A1 | 10/2007 | Nicolaescu et al. | |
| 2008/0266118 A1 | 10/2008 | Pierson et al. | |
| 2009/0188501 A1 | 7/2009 | Forsyth et al. | |
| 2009/0221888 A1 | 9/2009 | Wijesiriwardana | |
| 2010/0280331 A1 | 11/2010 | Kaufman et al. | |
| 2011/0102177 A1 | 5/2011 | Johnson | |
| 2012/0065486 A1 | 3/2012 | Imran | |

FOREIGN PATENT DOCUMENTS

| | | | |
|---|---|---|---|
| GB | 2439347 A | 12/2007 | |
| JP | 2011-245316 A | 12/2011 | |
| KR | 10-2012-0094857 A | 8/2012 | |
| WO | WO 86/01172 A1 | 2/1986 | |
| WO | WO 93/00134 A1 | 1/1993 | |
| WO | WO 2008/013506 A1 | 1/2008 | |
| WO | WO 2012/040254 A2 | 3/2012 | |

* cited by examiner

WIRELESS SKIN TEMPERATURE MEASUREMENTS IN DIVING

CROSS-REFERENCE TO RELATED PATENT APPLICATIONS

This patent application claims the benefit of U.S. Provisional Patent Application No. 61/731,140, filed Nov. 29, 2012, the entire teachings and disclosure of which are incorporated herein by reference thereto.

FIELD OF THE INVENTION

This invention generally relates to wireless measurements systems, and more particularly to wireless skin temperature measurement systems for use while diving.

BACKGROUND OF THE INVENTION

SCUBA and freedivers face a variety of dangers associated with these sporting activities. One such danger is decompression sickness that results from inert gas uptake during a dive. The amount of inert gas uptake is affected by the depth/pressure experienced over time by the diver. Dive computers have been used that employ diving decompression algorithms that track depth and time in order to determine dive stops in order to help avoid the danger of decompression sickness.

Further, physiological data from the diver can provide improved information to be utilized by the diving algorithm operating on a dive computer that determines dive time and decompression stop times and depth. For instance, the ZHL-8ADT model uses workload from a diver's heart rate to improve the diving algorithm. An example of a dive computer that utilizes heart rate information to improve a dive algorithm is found in U.S. Pat. No. 7,310,549 entitled Dive Computer with Heart Rate Monitor, assigned to Johnson Outdoors Inc., the entire teachings and suggestions of which are incorporated herein by reference thereto.

Another physiological data point that may be utilized to improve a diving algorithm is skin temperature. Skin temperature has an influence on a perfusion rate of the diver's body. The perfusion rate of various compartments of a diver's body during a dive will affect transfer of inert gases as well as metabolized oxygen within each compartment. During a typical dive, the perfusion rate determines how the inert gases are solving to tissues in the compartment at higher ambient pressures and dissolving when ambient pressure is decreased. Because the perfusion rate of a diver's skin is affected by skin temperature, a diving algorithm determining decompression parameters that does not take into account skin temperature is inefficient.

Further, a diver's skin forms the largest compartment exposed directly or indirectly to water during a dive. Water conducts heat approximately 20 times better than air, and as a result divers tend to protect themselves from excessive heat loss by wearing thermal isolating suits such as wet and dry suits. In wet suits, the isolation is based on water circulation not directly cooling skin, as a smaller amount of water is trapped between the suit and the skin such that the trapped water is raised in temperature and thereby acts as a buffer to the cooler water outside of the wet suit. In dry suits, the skin protected by the suit is separated from the water by a watertight barrier and body temperature is regulated by thermally protective undergarments.

Regardless of whether a diver utilizes a wet suit or a dry suit, the skin is generally covered. Therefore, dive computers that utilize skin temperature for improving a dive algorithm generally estimate the skin temperature based on surrounding water temperature and diver workload, which is typically estimated from the diver's heart rate or breathing rate.

A better way to determine skin temperature is a direct measurement from the skin of the diver. However, a direct measurement of skin temperature is difficult because a diver's skin is generally covered in order to protect the diver from the cooling effect of the water surrounding the diver's body. Therefore, what is needed is a method and device to directly measure skin temperature of a diver during a dive and provide that measurement data to a dive computer to utilize the skin temperature measurement in a diving algorithm in order to improve the diving experience.

The invention provides such a method and device to directly measure skin temperature of a diver during a dive and provide that measurement data to a dive computer to utilize the skin temperature measurement in a diving algorithm. These and other advantages of the invention, as well as additional inventive features, will be apparent from the description of the invention provided herein.

BRIEF SUMMARY OF THE INVENTION

In one aspect, the invention provides a dive computer system that includes a dive computer and a sensor. The dive computer has a display on which information is displayed and a processor. The sensor takes skin temperature measurements directly from the diver's skin and is operably coupled to the dive computer such that the skin temperature measurements can be supplied to the processor of the dive computer. The processor is configured to utilize a decompression algorithm to calculate dive parameters and the skin temperature measurements to compensate the decompression algorithm for diver skin temperature.

In an embodiment of the invention, the sensor is attached to a measurement device that includes a measurement device processor and a wireless transmitter. The measurement device processor applies a transmission coding to the heart rate measurements and the skin temperature measurements such that the heart rate measurements and the skin temperature measurements are transformed into a coded data. The transmission coding is based on a maximum and minimum diver heart rate. The wireless transmitter of the measurement device modulates the coded data to a higher frequency and wirelessly transmits the coded data to a receiver of the dive computer. The receiver demodulates the coded data to a baseband frequency and provides the coded data to the processor of the dive computer.

In another aspect, the invention provides a method of compensating a dive algorithm with diver skin temperature. The method includes measuring the skin temperature directly from the skin of a diver during a dive. Then the method transmits the measured skin temperature of the diver to a diver computer, and calculates an updated dive specific skin perfusion factor.

In an embodiment of the method of compensating a dive algorithm, the method calculates an updated half time for a skin compartment of the dive algorithm based on the updated dive specific skin perfusion factor and compares the updated dive specific skin perfusion factor to a previously stored skin perfusion factor. The method then increases a recommended ascent and decompression stop time if the updated dive specific skin perfusion factor has increased from the previously stored skin perfusion factor, and maintains or decreases a recommended ascent and decompression stop time if the updated dive specific skin perfusion factor has decreased from the previously stored skin perfusion factor.

In a further embodiment of the method of compensating a dive algorithm, the method determines an updated inert gas saturation within a skin compartment of the dive algorithm based on the updated dive specific perfusion factor, and then compares the updated inert gas saturation with a previously stored inert gas saturation of the skin compartment of the dive algorithm. The method then maintains or increases the skin compartment pressure tolerance if the updated inert gas saturation within the skin compartment has decreased from the previously stored inert gas saturation of the skin compartment, and decreases the skin compartment pressure tolerance if the updated inert gas saturation within the skin compartment has increased from the previously stored inert gas saturation of the skin compartment.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
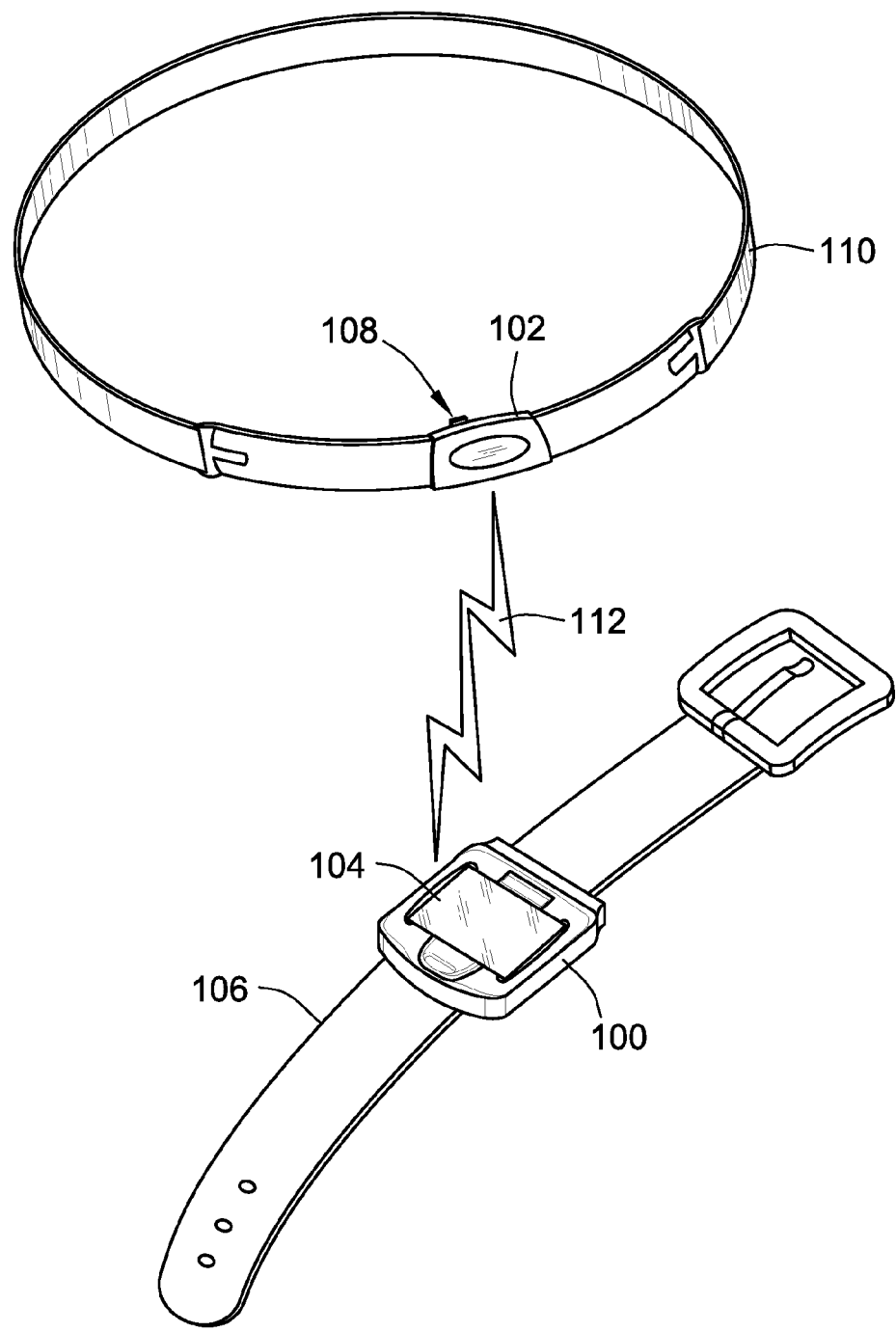
FIG. 1 illustrates one embodiment of a dive computer system of the present invention with a combined heart rate monitor and skin temperature measurement device.

FIG. 1 illustrates a dive computer 100 and a combination heart rate monitor and skin temperature measurement device 102. In the embodiment of the invention illustrated in FIG. 1, the measurement device 102 is wirelessly connected to the dive computer 100. While in the illustrated embodiment the connection is wireless, a wired connection is contemplated as well.

Measurement device 102 is configured to measure both a diver's heart rate and skin temperature and transmit a diver's physiological data that includes heart rate data and skin temperature data 112 to the dive computer 100. The measurement device includes a sensor 108 to take the preferred measurements from the diver. The sensor 108 is small enough such that it does not cause a localized warming effect to the skin where the measurement is being taken.

In the embodiment illustrated in FIG. 1, the measurement device 102 is attached to an attachment strap 110. Typically, heart rate measurements are performed on the diver's chest. As such, the attachment strap 110 is large enough to secure the measurement device 102 to a diver's chest.

Further, the measurement device 102 is worn under any thermal protection worn by the diver. In this manner, the measurement device 102 is capable of sensing a heart rate and taking a skin temperature measurement directly from the chest region of the diver. Correlations have shown that a single skin temperature measurement from the chest follows closely with skin temperature measurements from extremities of the body such as a wrist and ankle. As such, only a single measurement device 102 need be employed by a diver during a dive.

Further, accuracy for a single measurement device 102 located on the diver's chest may be improved by providing a type of thermal protection worn by the diver to the dive computer 100. Several styles of thermal protection are used by divers providing a range of protection. On the lighter protection side is the neoprene shorty, and on the heavier protection side is the dry suit. This information can be used by the dive computer 100 to better interpret skin temperature data 112 received from the measurement device 102.

Figure 2:
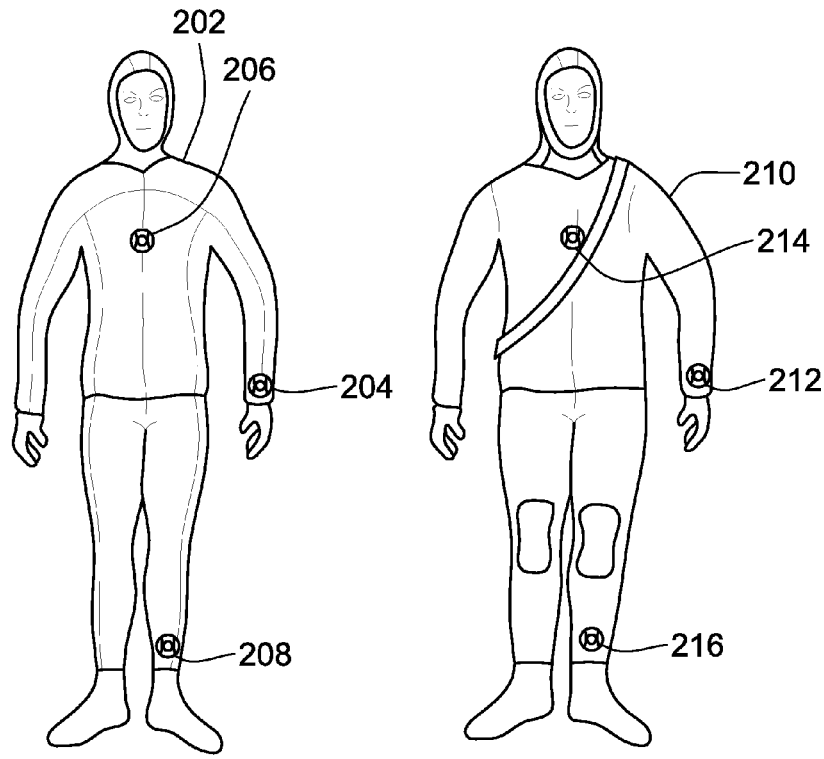
FIG. 2 is illustrates an embodiment of the present invention that includes more than a single skin temperature measurement device.

While typically only a single measurement device 102 is used, more than one device is contemplated, as illustrated in FIG. 2, which includes diver 202 and diver 210. Each diver 202 and 210 are wearing a different style of thermal protection, but each have a first measurement device 206, 214, a second measurement device 204, 212, and a third measurement device 208, 216.

Figure 3:
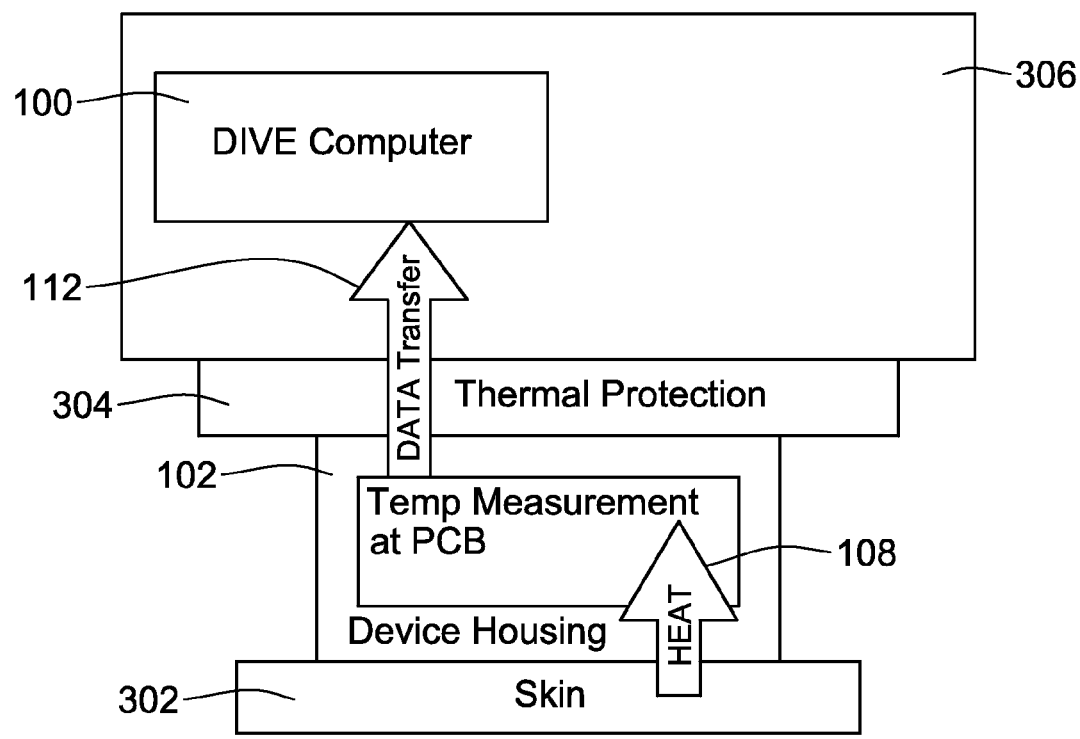
FIG. 3 is an illustration of heat conduction and data transmission according to an embodiment of the present invention.

FIG. 3 illustrates a block diagram of the skin temperature measurement. The measurement device 102 is situated directly against the diver's skin such that heat emanating from the surface of the diver's skin is measured by sensor 108, which is in direct contact with the diver's skin. This skin temperature measurement is then transmitted from the measurement device 102 through the diver's thermal protection 304 and the water 306 to the dive computer 100. The dive computer 100 then makes use of the skin temperature measurement in determining dive parameters.

Figure 4:
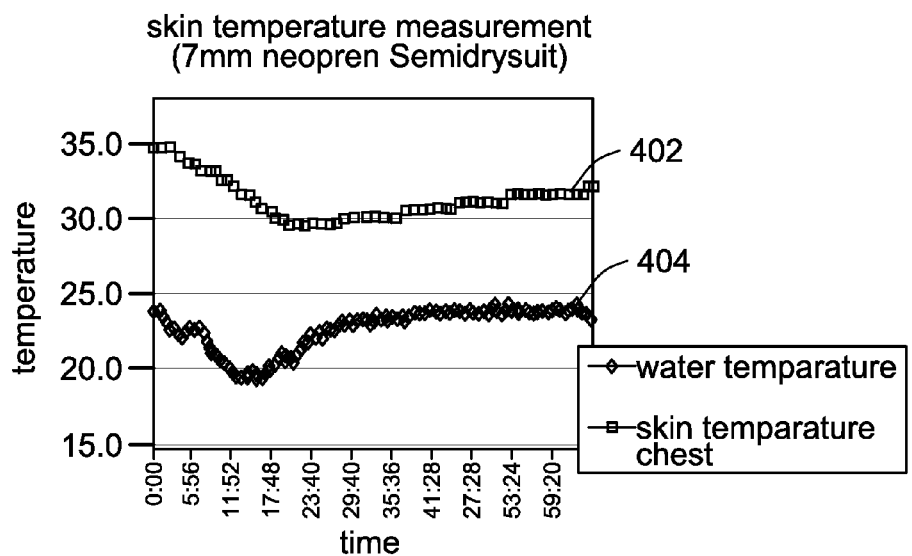
FIG. 4 illustrates a comparison of measured water temperature and measured skin temperature during a dive.

Typically, as illustrated in the graph of FIG. 4, a diver's skin temperature correlates to the water temperature. This is seen in FIG. 4 by comparing the skin temperature curve 402 to the water temperature curve 404. The temperature data points were taken over time during a dive with the diver wearing a 7 mm neoprene semidry suit.

However, some differences can also be seen between the skin temperature curve 402 and the water temperature curve 404. For instance, the slope of the curve between the start time and the 17:48 time marking is steeper for the water temperature 404 than the for the skin temperature curve 402, and the subsequent temperature increase is more significant for the water temperature curve 404 than for the skin temperature curve 402. As such, the correlation between the skin temperature 402 and water temperature 404 during a dive is not exact. Therefore, the measurement device 102 must avoid introducing excess heat or cold to the measurement prior to or during the measurement. A preferred method of avoiding adding excess heat or cold is to transmit the measured data 112 (see FIG. 1) wirelessly.

Figure 5A:
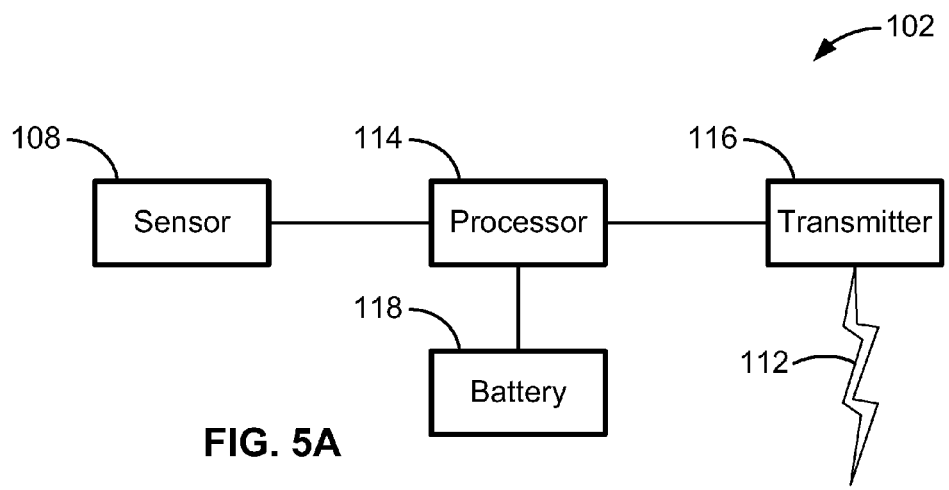
FIG. 5A illustrates a block diagram of a combined heart rate monitor and skin temperature measurement device, in accordance with an embodiment of the present invention.
Figure 5B:
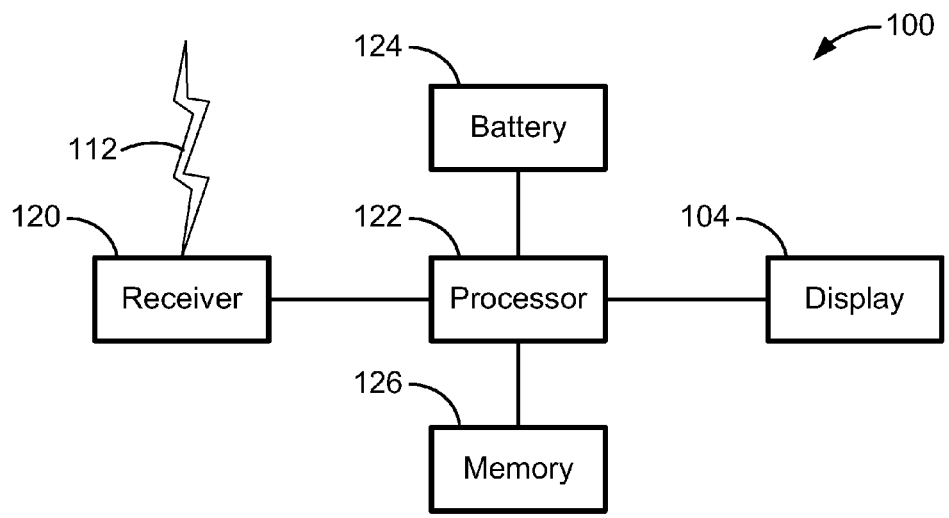
FIG. 5B illustrates a block diagram of a dive computer, in accordance with an embodiment of the present invention.

FIG. 5A and FIG. 5B illustrate a block diagram of the measurement device 102 and the dive computer 100, respectively, that are capable of wireless communication. FIG. 5A illustrates a measurement device 102 powered by a battery 118. The measurement device 102 includes the sensor 108 that takes a skin temperature and heart rate measurement and provides that data to a processor 114. The processor 114 applies a coding scheme (discussed later in relation to FIG. 6) to the heart rate and skin temperature data and sends that to a wireless transmitter 116. Wireless transmitter 116 modulates the baseband measurement data to a higher carrier frequency, typically within the VLF bandwidth, to be transmitted as wireless measurement data 112.

FIG. 5B illustrates a block diagram of a battery 124 powered dive computer 100. The wireless measurement data 112 sent from the measurement device 102 is received by the dive computer 100 at a receiver 120. The receiver 120 down converts the wireless data 112 back down to a baseband signal and passes that to a processor 122. The processor 122 decodes the baseband signal in order to extract the heart rate and skin temperature measurement data 112. Further, that measurement data 112 may be stored in a memory device 126 for later use, or used immediately by the processor 122. Typically, the measurement data 112 will be used to compensate a dive algorithm (discussed later in relation to FIG. 7) running on the processor 122. The result of this compensation to the dive algorithm will be displayed on a display 104 for the diver to interpret.

As previously mentioned, the baseband signal is modulated up to the VLF (very low frequency) bandwidth. The VLF bandwidth is desirable because of the fact that the measurement device 102 and dive computer 100 are primarily used under water. A drawback to the VLF bandwidth is that it typically has a significant amount of noise that can cause interference. To overcome this interference a coding scheme is applied to the measurement data 112. The coding scheme is known by the dive computer 100 such that the measurement data 112 can be decoded at the dive computer 100.

While several coding schemes could potentially be used, a scheme that takes advantage of the physical limitations of the data to be transmitted is desirable. For instance, the measurement data 112 includes heart rate and skin temperature data. The human heart typically has a minimum rate of 25-30 beats per minute and a maximum rate of 220-240 beats per minute. In the desired coding scheme, a set of pulses are transmitted in a fixed pattern repeated at every heartbeat. As such, the above defined physical limits of the human heart rate define windows of time where further heartbeats are not possible.

Therefore, no more than one set of pulses should be transmitted and/or received in any 270 ms window of time. 270 ms represents the window of time for a single heartbeat at a heart rate of 220 beats per minute. Also, on the opposite end of the heart rate spectrum, no fewer than one set of pulses should be received in any window of time greater than 500 ms, which represents the time for a single heartbeat at a heart rate of 30 beats per minute. As such, data received that is outside of these time limits will be rejected during the decoding process at the processor 122 of the dive computer 100.

In this manner, the quantity of the set of pulses received at the receiver 120 (see FIG. 5B) over a specific period of time will provide the heart rate data. Further, because the skin temperature does not change more rapidly than the heart rate, the skin temperature data can be sent along with each set of pulses indicating the heart rate. The received skin temperature data can then be averaged to obtain an accurate skin temperature. Additionally, this scheme allows the measurement device 102 to be backwards compatible with other dive computers that are only equipped to handle heart rate information and not skin temperature.

Figure 6:
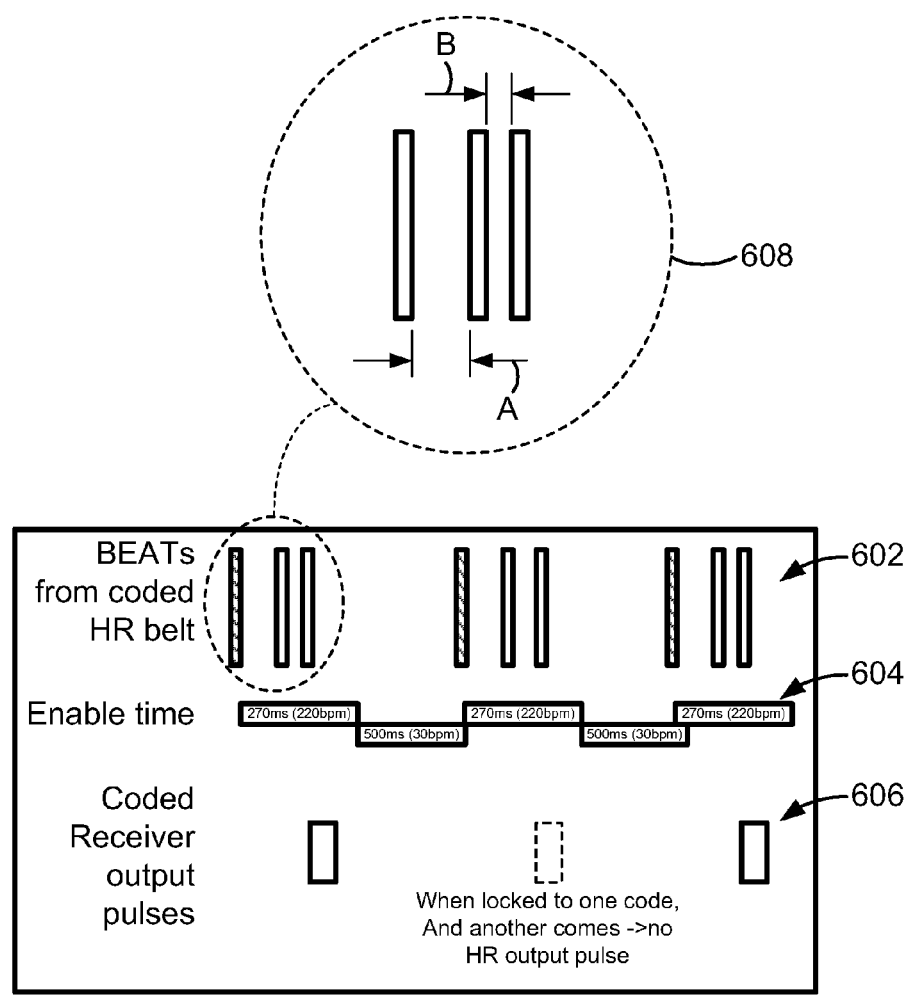
FIG. 6 illustrates a wireless coding principle for wireless data transmission, in accordance with an embodiment of the present invention.

FIG. 6 illustrates the wireless coding principle described. Specifically, FIG. 6 illustrates a series of pulses that form coded beats 602 from the measurement device 102 sent during an enable window time 604 that is developed based on the maximum and minimum heart rate. Further, an output pulse train 606 is shown, which is an output from the processor 122 (see FIG. 5B) to memory 126 that contains heart rate and temperature data 112. The memory 126 stores these values in order for the processor 122 to then determine the heart rate and skin temperature of the diver.

The set of pulses transmitted every heartbeat and containing skin temperature is coded such that the receiver 120 (see FIG. 5B) can train onto the coded pulses in order to reject pulses that do not fit the code. This skin temperature coding can be accomplished in several ways. One such way is a direct time to temperature value coding:

$$T_{(skin)} = \text{min value} + \Delta A \quad (B \text{ is constant}) \tag{1}$$

$$T_{(skin)} = \text{min value} + \Delta B \quad (A \text{ is constant}) \tag{2}$$

$$T_{(skin)} = 10 * \Delta A + \Delta B \quad (\text{with decade information at } A) \tag{3}$$

The above set of equations (1)-(3) create a spacing between the pulses of $\Delta A$ and $\Delta B$, as illustrated in the close up image of the set of pulses 608. The dive computer 100 can be trained to recognize the set of pulses from a specific measurement device 102 because at startup the receiver 120 has a learning phase in which it locks to a specific code and allows only a defined variation over time. In this way, the maximum temperature range of the skin is defined.

Equations (1)-(3) take advantage of the fact that during a dive a diver's skin temperature will not go below 18° C. or above 36° C., as these are physical limits at which a diver will develop either hypothermia or heat exhaustion. As such, a coding scheme that defines either $\Delta A$ and/or $\Delta B$ as incremental temperature steps that add to a minimum (or maximum) temperature value in order to define a measured skin temperature has been developed.

In an embodiment of the invention using equation (1) above, min value could be defined as 18° C. and $\Delta A$ could be defined as a 1° C. incremental step. As such, if skin temperature is measured to be 35° C., then the $\Delta A$ would create a spacing indicating a 17° C. incremental spacing. Further, using equation (1) B, from FIG. 6, would be held constant. The processor 122 at the dive computer 100 (see FIG. 5B) would interpret the spacing in the series of pulses forming the measurement data 112 as the measured 35° C. skin temperature.

In an embodiment of the invention using equation (2) above, min value could be defined as 18° C. and $\Delta B$ could be defined as a 1° C. incremental step. As such, if skin temperature is measured to be 35° C., then the $\Delta B$ would create a spacing indicating a 17° C. incremental spacing. Further, using equation (2) A, from FIG. 6, would be held constant. The processor 122 at the dive computer 100 (see FIG. 5B) would interpret the spacing in the series of pulses forming the measurement data 112 as the measured 35° C. skin temperature.

In an embodiment of the invention using equation (3) above, no min value is needed. No min value is needed because the temperature value can be specified by assigning an incremental value to both ΔA and ΔB. For instance, as shown in equation (3), both ΔA and ΔB could be defined in 1° C. incremental steps. Further, ΔA could be multiplied by 10 in order for ΔA to represent decade temperature measurements. Please note that this could be done using ΔB as well. As such, if skin temperature is measured to be 35° C., then a series of pulses, as shown in FIG. 6, would be developed where ΔA creates a spacing indicating a 3° C. incremental step and ΔB creates a spacing indicating a 5° C. incremental step. The processor 122 at the dive computer 100 (see FIG. 5B) would interpret the spacing in the series of pulses forming the measurement data 112 as the measured 35° C. skin temperature.

Furthermore, if more than one person in a dive group on a dive is using a measurement device 102, an individual diver computer 100 will be able to distinguish between the two measurement devices 102. This is possible because, using the above coding scheme, two identical same codes would be rare when using skin temperature as a base. This is illustrated in the second set of pulses of the coded beats 602. In this second set of pulses the ΔB is larger, and as such, represents too large of a shift in skin temperature to be caused naturally. As a result, the processor 122 of the dive computer 100 does not send out an output pulse containing measurement information, as shown in the pulse train 606.

In this manner, measurement data 112 including heart rate data and skin temperature data is provided to the dive computer 100 to compensate a dive algorithm that monitors dive parameters in order to alert the diver on time of dive and length of ascent times and decompression stop depths and times to avoid decompression sickness.

Figure 7:
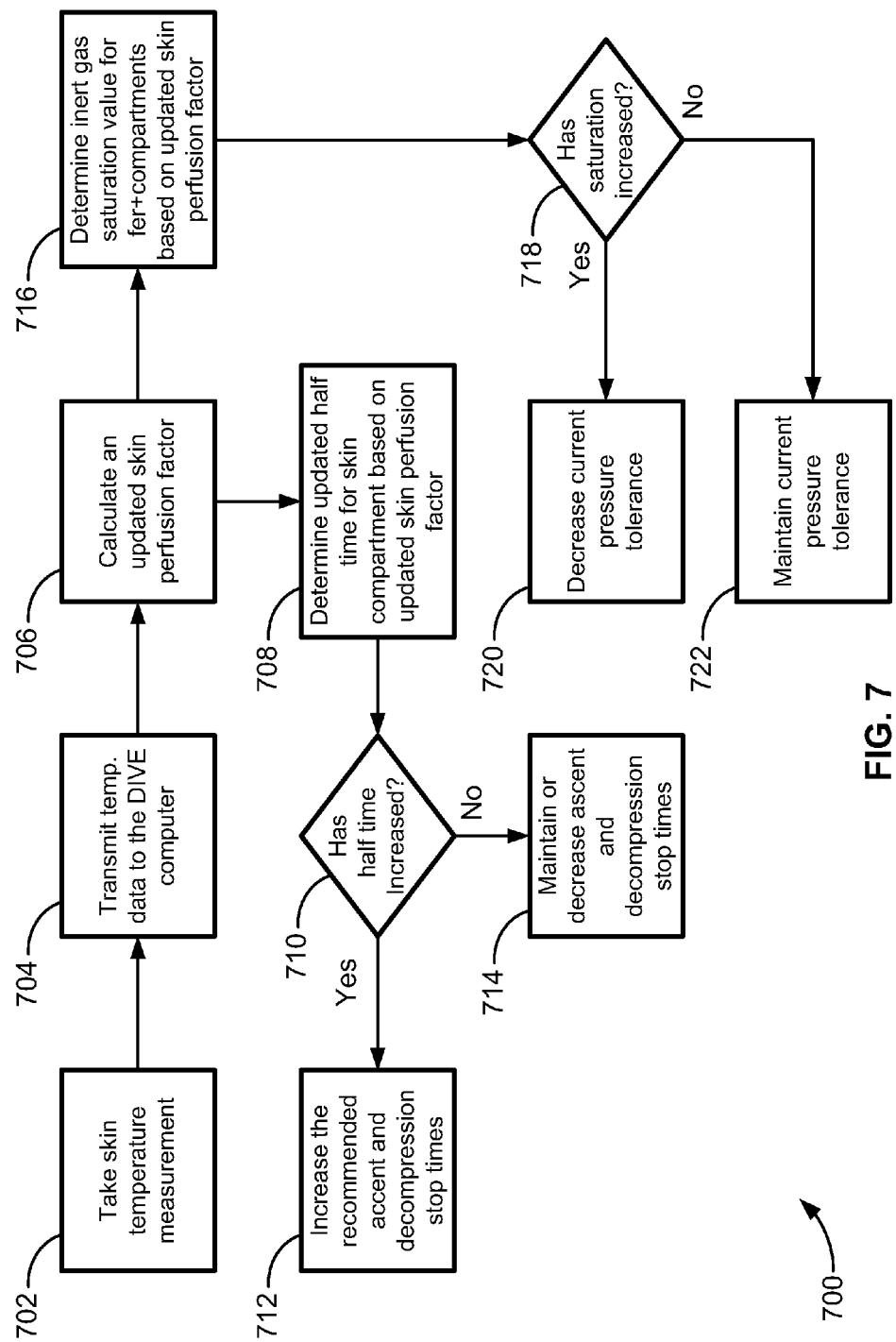
FIG. 7 illustrates a dive algorithm flow chart that takes skin temperature into account, in accordance with an embodiment of the present invention.

FIG. 7 illustrates the use of skin temperature to compensate a dive algorithm 700. Skin decompression sickness is the most common form of decompression sickness. A combination of heart rate data and skin temperature data allows the algorithm 700 to accurately determine dive parameters in order to customize a dive such that the diver will not develop decompression sickness.

A skin compartment, just like any other compartment within the body, will saturate with a gas when the partial pressure of the breathed gas is higher than the partial pressure of the skin compartment. Also, the skin compartment will desaturate when the breathed gas partial pressure is lower than the partial pressure at the skin compartment. The skin compartment can tolerate a certain amount of overpressure before bubble formation begins, which leads to decompression sickness. The amount of overpressure the skin compartment can take depends on the skin compartment halftime, which is modified by the skin blood perfusion rate.

Skin compartment saturation, just like any other compartment saturation, is nonlinear and uses half times to determine a length of time at a lower pressure required to desaturate. Typically, the skin compartment will have a half time of 40, 80, or 160 minutes. The half time of the skin compartment, or any other compartment, will change with the formula:

$$T_j = T_j^N \left(\frac{n_{Bj}}{n_{Bj}^N}\right)^{-0.5\left(1-\frac{n_{Bj}}{n_{BJ}^N}\right)} \quad (4)$$

where T is a specific half time and $n_{Bj}$ is the corresponding perfusion rate for the particular compartment. The perfusion rate $n_{Bj}$ is affected by temperature according to the following formula:

$$n_{Bj} = n_{Bj}^N + \text{Temperature} * dn_{Bj}^T \quad (5)$$

Where $dn_{Bj}^T$ is a compartment temperature correlation factor.

FIG. 7 illustrates a dive algorithm 700 that takes into account the effect of skin temperature on the skin compartment perfusion rate in both the inert gas saturation and desaturation of the skin compartment. At block 702, the measurement device 102 (see FIG. 1) takes a skin temperature measurement and transmits that measurement to the dive computer 100 at block 704. The dive computer 100 uses the skin temperature measurement to calculate an updated skin perfusion factor at block 706. Next, when determining skin desaturation, algorithm 700 proceeds to block 708 where an updated half time for the skin compartment is calculated. This updated half time is based on the updated skin perfusion factor calculated at block 706. Next, the dive algorithm 700 proceeds to question block 710 where the updated half time calculated at block 708 is compared to the previous half time. If the result of the comparison shows that the half time has increased, then the dive computer 100 increases the recommended ascent and decompression stop times at block 712. If the result of the comparison shows that the half time has decreased, then the dive computer 100 either maintains or decreases the ascent and decompression stop times, at block 714.

If the dive algorithm is determining skin saturation, then after block 706 the dive algorithm 700 proceeds to block 716 where inert gas saturation is determined based on the updated perfusion factor. The temperature change of the skin compartment affects saturated tissue due to micro bubble formation from a blood circulation change. In this scenario, the blood moves the bubbles that have formed in the cavities of the compartments. Therefore, an increased perfusion rate indicates a decrease in the tolerance for a particular compartment to tolerate an increased pressure. Further, a decreased perfusion rate indicates an increase in the compartments pressure tolerance. This process is captured at question block 718 where the dive algorithm 700 asks if inert gas saturation has increased. If inert gas saturation has increased, then the dive algorithm 700 proceeds to block 720 where the pressure tolerance for that compartment is decreased. If the inert gas saturation has decreased, then the dive algorithm 700 proceeds to block 722 to either maintain the pressure tolerance or increase the pressure tolerance.

Furthermore, while dive algorithm 700 is primarily intended to be used during a dive to determine dive parameters such as ascent time, decompression stop time, and compartment pressure tolerance, skin temperature measurements can continue to be made once the diver has exited the water as well. The desaturation determination that calculates a half time based on skin temperature at block 708 can still be ran until the slowest compartment has reached equilibrium with the ambient pressure. In this manner, the dive computer 100 can continue to inform the diver of skin perfusion rate as the diver's body continues to decompress after the dive.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A dive computer system, comprising:
   a dive computer having a display on which information is displayed and a processor; and
   a sensor that takes skin temperature measurements directly from the diver's skin, the sensor is operably coupled to the dive computer such that the skin temperature measurements can be supplied to the processor of the dive computer from the sensor, the processor is configured to utilize a decompression algorithm to calculate dive parameters and the skin temperature measurements to compensate the decompression algorithm for diver skin temperature,
   wherein the sensor also takes heart rate measurements in addition to the skin temperature measurements, and
   wherein the sensor is attached to a measurement device that includes a measurement device processor and a wireless transmitter, the measurement device processor applies a transmission coding to the heart rate measurements and the skin temperature measurements such that the heart rate measurements and the skin temperature measurements are transformed into a coded data, the transmission coding is based on a diver heart rate and a diver skin temperature, the transmitter modulates the coded data to a higher frequency and wirelessly transmits the coded data to a receiver of the dive computer; the receiver demodulates the coded data to a baseband frequency and provides the coded data to the processor of the dive computer.

2. The dive computer system of claim 1, wherein the sensor is in direct contact with a diver's skin.

3. The dive computer system of claim 1, wherein the sensor is embedded in a measurement device and attached to a strap that is worn on a diver's chest.

4. The dive computer system of claim 1, wherein the transmitter modulates the coded data to a carrier frequency within a VLF spectrum.

5. A method of compensating a dive algorithm with diver skin temperature, comprising the steps of:
   measuring the skin temperature directly from the skin of a diver during a dive;
   transmitting the measured skin temperature of the diver to a diver computer; and
   calculating an updated dive specific skin perfusion factor.

6. The method of compensating a dive algorithm of claim 5, further comprising the steps of:
   calculating an updated half time for a skin compartment of the dive algorithm based on the updated dive specific skin perfusion factor;
   comparing the updated dive specific skin perfusion factor to a previously stored skin perfusion factor;
   increasing a recommended ascent and decompression stop time if the updated dive specific skin perfusion factor has increased from the previously stored skin perfusion factor; and
   maintaining or decreasing a recommended ascent and decompression stop time if the updated dive specific skin perfusion factor has decreased from the previously stored skin perfusion factor.

7. The method of compensating a dive algorithm of claim 5, further comprising the steps of:
   determining an updated inert gas saturation within a skin compartment of the dive algorithm based on the updated dive specific perfusion factor;
   comparing the updated insert gas saturation with a previously stored inert gas saturation of the skin compartment of the dive algorithm;
   maintaining or increasing the skin compartment pressure tolerance if the updated inert gas saturation within the skin compartment has decreased from the previously stored inert gas saturation of the skin compartment; and
   decreasing the skin compartment pressure tolerance if the updated inert gas saturation within the skin compartment has increased from the previously stored inert gas saturation of the skin compartment.

8. The method of compensating a dive algorithm of claim 5, wherein the step of transmitting the measured skin temperature of the diver to a diver computer is done wirelessly.

* * * * *